United States Patent [19]
Woiszwillo et al.

[11] Patent Number: 5,554,730
[45] Date of Patent: Sep. 10, 1996

[54] METHOD AND KIT FOR MAKING A POLYSACCHARIDE-PROTEIN CONJUGATE

[75] Inventors: James E. Woiszwillo, Milford; Jie Di, Norwood, both of Mass.

[73] Assignee: Middlesex Sciences, Inc., Norwood, Mass.

[21] Appl. No.: 372,820

[22] Filed: Dec. 23, 1994

Related U.S. Application Data

[63] Continuation-in-part of Ser. No. 206,456, Mar. 4, 1994, which is a continuation-in-part of Ser. No. 28,237, Mar. 9, 1993, abandoned.

[51] Int. Cl.$^6$ ............ C07K 17/02; A61K 39/02; A61K 39/05; A61K 39/095
[52] U.S. Cl. ............ 530/410; 530/350; 424/234.1; 424/236.1; 424/245.1; 424/250.1
[58] Field of Search ............ 530/410, 350; 424/256.1, 245.1, 250.1, 236.1, 234.1, 241.1, 257.1, 244.1, 259.1, 261.1, 260.1

[56] References Cited

U.S. PATENT DOCUMENTS

| | | | |
|---|---|---|---|
| 3,838,007 | 9/1974 | van Velzen | 435/96 |
| 4,115,534 | 9/1978 | Ithakissios | 436/500 |
| 4,169,804 | 10/1979 | Yapel | 252/62.53 |
| 4,356,170 | 10/1982 | Jennings et al. | 424/194.1 |
| 4,496,689 | 1/1985 | Mitra | 525/54.1 |
| 4,663,160 | 5/1987 | Tsay et al. | 424/87 |
| 4,693,891 | 9/1987 | Collins et al. | 424/92 |
| 4,771,127 | 9/1988 | Cryz et al. | 530/395 |
| 4,822,535 | 4/1989 | Ekman et al. | 264/4.3 |
| 4,863,972 | 9/1989 | Itagaki et al. | 521/141 |
| 4,902,506 | 2/1990 | Anderson et al. | 424/92 |
| 5,204,098 | 4/1993 | Szu et al. | 424/194.1 |
| 5,425,946 | 1/1995 | Tai et al. | 424/197.11 |

FOREIGN PATENT DOCUMENTS

| | | |
|---|---|---|
| 0106495A3 | 4/1984 | European Pat. Off. . |
| 0414223A2 | 2/1991 | European Pat. Off. . |
| A86223230 | of 0000 | Japan . |
| 2002319 | 2/1979 | United Kingdom . |
| 2079937 | 7/1992 | United Kingdom . |
| PCT/US93/00073 | 1/1993 | WIPO . |
| WO93/14110 | 7/1993 | WIPO . |

OTHER PUBLICATIONS

Carrell, S., "Novel Systems for Drug Delivering Biotechnology Drugs Explored," *Genetic Engineering News*, pp. 2, 10 (Feb. 1993).

Danishefsky, S., "Catalytic Antibodies and Disfavored Reactions," *Science*, col. 259, pp. 469–470 (1993).

Farrugia et al., "Studies on the Procurement of Coagulation Factor VIII: Selective Precipitation of Factor VII with Hydrophilic Polymers," *Thromb. Haemostas*, vol. 51, No. 3, pp. 338–342 (1984).

Harris et al., "Therapeutic Antibodies—The Coming Age," *Tib Tech*, vol. 11, pp. 42–44 (Feb. 1993).

Madhusudhan et al. "Modification of Enzyme Activity in Reveresed Micelles Through Clathrate Hydrate Formulation," *Biotechnol. Prog.*, vol. 6, pp. 465–471 (1990).

Phillips et al., "Protein Recovery from Reversed Micellar Solutions through Contact with a Pressurized Gas Phase," *Biotechnol. Prog.*, vol. 7, pp. 43–48 (1991).

Suelter, C. H., *A Practical Guide to Enzymology*, John Wiley & Sons, pp. 78–87 (1986).

Taylor, R., "Expanding Applications in the Food Industry for Immobilized Enzymes," *Genetic Eng. News*, p. 5, (Feb. 1993).

Waldman, T. A., "Monoclonal Antibodies in Diagnosis and Therapy," *Science*, vol. 252, pp. 1657–1662 (1991).

Whitman et al., "Purified Viruses and Viral Proteins," (Name of Journal Unknown).

Goodman–Snitkoff et al., *J. Immunol.*, vol. 147, pp. 410–415 (1991).

Miller et al., *J. Exp. Med.*, vol. 176, pp. 1739–1744 (1992).

Kreuter, J., Microcapsules and Nonparticles in Medicine and Pharmacology, M. Donbrow (ed.), CRC Press, pp. 125–148.

Eldridge et al., *Current Topics in Microbiology and Immunology*, vol. 146, pp. 59–66 (1989).

*Primary Examiner*—George C. Elliott
*Assistant Examiner*—Nancy J. Degen
*Attorney, Agent, or Firm*—Jones & Askew

[57] ABSTRACT

A method and kit for making a polysaccharide-protein Schiff base conjugate. A polysaccharide is oxidized with an oxidizing agent and combined with a protein in the presence of a macromolecular crowding agent to form a Schiff base. Preferably, the macromolecular crowding agent is a soluble linear polymer selected from the group consisting of polyvinylpyrrolidone, polyethylene glycol, dextran, nonylphenol-ethoxylates, polyvinyl alcohol, and mixtures thereof. Most preferably, the macromolecular crowding agent is a mixture of polyvinylpyrrolidone and polyethylene glycol. The microparticles or substantially dissolved microparticles are immunogenic and are useful for inducing an immune response when administered to humans or animals.

30 Claims, No Drawings

5,554,730

METHOD AND KIT FOR MAKING A POLYSACCHARIDE-PROTEIN CONJUGATE

CROSS-REFERENCE RELATED APPLICATIONS

This is a continuation-in-part of U.S. patent application Ser. No. 08/206,456, filed Mar. 4, 1994, which is a continuation-in-part of pending U.S. patent application Ser. No. 08/028,237, filed Mar. 9, 1993, now abandoned.

FIELD OF THE INVENTION

This relates to the field of biochemistry and more particularly relates to polysaccharide-protein conjugates.

BACKGROUND OF THE INVENTION

Infants are routinely given a series of vaccinations within the first few months of life to confer protection against potentially life-threatening bacterial and viral diseases. Some antigens, especially the carbohydrate antigens of bacteria, fail to induce a protective immune response in infants. These antigens must be administered with a protein carrier to stimulate an immune response. For example, an antigen such as the capsular polysaccharide of *Haemophilus influenzae* type b (Hib), the bacteria primarily responsible for bacterial meningitis, must be conjugated to a carrier protein for successful induction of an antibody response in infants.

A variety of chemical linkages have been used to prepare polysaccharide-protein conjugates. However, the coupling methods employed are time-consuming and result in linkages, such as amido linkages, that cause excessive crosslinking or detrimental modifications to the antigen, which are undesirable in human vaccines. For example, polysaccharides may be coupled to proteins using reductive amination as described in U.S. Pat. No. 4,356,170 to Jennings et al., entitled "Immunogenic Polysaccharide-Protein Conjugates". Conjugation is achieved by oxidizing the polysaccharide with an oxidizing agent, coupling the oxidized polysaccharide to a protein, and reducing the bond with a reducing agent for stability. This process requires lengthy dialysis and incubation steps and chromatography purification and may take up to two to three weeks for completion.

What is needed is a rapid, inexpensive polysaccharide-protein conjugation method that results in a stable conjugate capable of conferring an immune response that renders protection against microbial infections, especially in human infants.

SUMMARY OF THE INVENTION

A method for preparing an immunogenic polysaccharide-protein conjugate is provided. In accordance with the method, a polysaccharide is first oxidized with an oxidizing agent. The oxidizing agent is preferably a glycol cleaving agent such as tetra-acetate. periodic acid, or sodium periodate. A protein is then added to the oxidized polysaccharide, and the polysaccharide and protein are coupled in the presence of a macromolecular crowding agent to form a Schiff base. Preferably, the macromolecular crowding agent is a soluble linear polymer selected from the group consisting of polyvinylpyrrolidone, polyethylene glycol, dextran, nonylphenol-ethoxylates, polyvinyl alcohol, and mixtures thereof. Most preferably, the macromolecular crowding agent is a mixture of polyvinylpyrrolidone and polyethylene glycol. The oxidized polysaccharide, protein, and macromolecular crowding agent are incubated together for a sufficient amount of time at a predetermined temperature until the formation of microparticles.

The microparticles are composed of polysaccharide-protein Schiff base conjugates. These microparticles are immunogenic and may be administered to humans and other animals by methods well known to those skilled in the art to induce an immune response. Alternatively, the microparticles are removed from the solution and substantially dissolved with an alkaline solution, yielding a composition containing both a soluble immunogenic polysaccharide-protein Schiff base conjugate and a small quantity of inmunogenic, slow-releasing microparticles.

The present invention also includes kits for preparing the polysaccharide-protein Schiff base conjugates. The kit can be in any configuration well known to those of ordinary skill in the art. Preferably, the kit contains an oxidizing agent for oxidation of the polysaccharide, a protein carrier, and a macromolecular crowding agent. The oxidizing agent is preferably a glycol cleaving agent such as tetra-acetate, periodic acid, or sodium periodate. The macromolecular crowding agent is preferably a soluble linear polymer selected from the group consisting of polyvinylpyrrolidone, polyethylene glycol, dextran, nonylphenol-ethoxylates, polyvinyl alcohol, and mixtures thereof. Most preferably, the macromolecular crowding agent is a mixture of polyvinylpyrrolidone and polyethylene glycol.

Useful polysaccharides include, but are not limited to, those derived from *Haemophilus influenza*, pneumococci, meningococci, β-hemolytic streptococci, *Escherichia coli*, *Pseudomonas aeruginosa*, Klebsiella, and *Vibrio cholerae*. Preferred proteins include, but are not limited to, tetanus toxoid, diphtheria toxoid, *Neisseria meningitidis* outer membrane protein, nontoxic cross-reacting mutant of diphtheria toxin, a protein derived from bacteria, or a synthetic protein containing lysine residues.

Accordingly, it is an object of the present invention to provide a rapid, inexpensive method for the preparation of polysaccharide-protein conjugates.

It is a further object of the present invention to provide a method for the preparation of stable, immunogenic polysaccharide-protein conjugates.

DETAILED DESCRIPTION OF THE INVENTION

The term "Schiff base" is defined herein as any of a class of derivatives of the condensation of aldehydes with primary amines.

A method for making a polysaccharide-protein conjugate by combining an oxidized polysaccharide with a protein in the presence of a macromolecular crowding agent is described herein. Preferably, the conjugate is immunogenic and is useful as a vaccine. Alternatively, the conjugate is useful for in vitro research and diagnostics wherein the protein portion of the polysaccharide-protein conjugate is labeled with a detectable label, such as fluorescein or a radiolabel, in accordance with methods well known to those skilled in the art, and the labeled conjugate is added to a biological sample or cell culture for the analysis of polysaccharide structure and function. Most preferably the conjugate is useful as a pediatric vaccine for the immunization of human infants. Alternatively, the conjugate may be used as a veterinary vaccine for the immunization of young animals.

The polysaccharide of the protein-polysaccharide conjugate is one that includes an oxidizable terminal aldehyde group capable of reacting with an amino group of a protein to form a Schiff base. The polysaccharide is preferably a bacterial antigen capable of inducing an immune response when coupled to a protein carrier. Useful polysaccharides include, but are not limited to, those derived from *Haemophilus influenza*, pneumococci, meningococci, β-hemolytic streptococci, *Escherichia coli, Pseudomonas aeruginosa*, Klebsiella, and *Vibrio cholerae*. Most preferably, the polysaccharide is one that is incapable of inducing an effective immune response in infants when administered alone, but produces a T lymphocyte-dependent immune response when coupled to a protein carrier and administered to infants. The protein may be any physiologically tolerated protein having a free amino group. Preferred proteins include, but are not limited to, tetanus toxoid, diphtheria toxoid, *Neisseria meningitidis* outer membrane protein, non-toxic cross-reacting mutant of diphtheria toxin, a protein derived from bacteria, or a synthetic protein containing lysine residues. The protein may be derived from the same source as the polysaccharide.

In accordance with the method, the polysaccharide is oxidized by incubating the polysaccharide with an oxidizing reagent. Preferably, the incubation is performed at room temperature for a sufficient amount of time to cause oxidation, most preferably between 15 and 45 minutes. The oxidizing agent may be any glycol cleaving agent capable of introducing an aldehyde. Preferably, the glycol cleaving agent is an oxidizing agent such as lead tetra-acetate, periodic acid, or sodium periodate. Most preferably, the glycol cleaving agent is sodium periodate. The glycol cleaving agent is then quenched by the addition of a quenching reagent. Preferably, the quenching reagent is an alcohol containing a gem-hydroxyl group such as ethylene glycol.

The protein is added to the oxidized polysaccharide reaction mixture and incubated in the presence of a macromolecular crowding agent. The macromolecular crowding agent may be added to the polysaccharide either before or after the addition of the protein.

A macromolecular crowding agent is defined herein as a compound that attracts water and allows molecules to aggregate. Preferably, the macromolecular crowding agent is a soluble, linear polymer such as polyvinylpyrrolidone or polyethylene glycol or a polymer mixture thereof. Such a polymer mixture may be prepared in accordance with the methods set forth in co-pending U.S. patent application Ser. No. 07/817,610 filed Jan. 7, 1992 by James E. Woiszwillo, U.S. Pat. No. 5,525,519, or PCT patent application No. 93–00073, WOg3/14110, filed Jan. 7, 1993 by James E. Woiszwillo, both of which are incorporated herein by reference. It will be understood by those skilled in the art that other soluble, linear polymers, such as dextran, nonylphenol-ethoxylates, polyvinyl alcohol, and mixtures thereof could be used in addition to PVP and PEG or in place of either PVP or PEG.

PVP is a non-ionogenic, hydrophilic polymer having a mean molecular weight ranging from approximately 10,000 to 700,000 and the chemical formula $(C_6H_9NO)_n$. PVP is also known as poly[1-(2-oxo-1-pyrrolidinyl)ethylene], Povidone™, Polyvidone™, RP 143™, Kollidon™, Peregal ST™, Periston™, Plasdone™, Plasmosan™, Protagent™, Subtosan, and Vinisil™. PVP is non-toxic, highly hygroscopic and readily dissolves in water or organic solvents.

Polyethylene glycol (PEG), also known as poly(oxyethylene) glycol, is a condensation polymer of ethylene oxide and water having the general chemical formula $HO(CH_2CH_2)_nH$.

Dextran is a term applied to polysaccharides produced by bacteria growing on a sucrose substrate. Native dextrans produced by bacteria such as *Leuconostoc mesenteroides* and *Lactobacteria dextranicum* usually have a high molecular weight.

Nonylphenol-ethoxylates (NPEs) are a class of long chained compounds often used as surfactants. They are usually derivatized to meet the desired solubility requirements.

Polyvinyl alcohol (PVA) is a polymer prepared from polyvinyl acetates by replacement of the acetate groups with hydroxyl groups and has the formula $(CH_2CHOH)_n$. Most polyvinyl alcohols are soluble in water.

PEG, dextran. PVA and PVP are commercially available from chemical suppliers such as the Sigma Chemical Company (St. Louis, Mo.). NPEs require custom synthesis and can be ordered from special chemical producers.

Most preferably, the macromolecular crowding agent is polymer mixture containing an aqueous solution of PVP having a molecular weight between 10,000 and 360,000, most preferably 40,000, and PEG having a molecular weight between 200 and 35,000, most preferably 3500. A polymer mixture of PVP having a molecular weight of 40,000 and PEG having a molecular weight of 3500 is the preferred macromolecular crowding agent. Preferably, the PVP is dissolved in an acetate buffer and PEG is added to the aqueous PVP solution. The concentration of each polymer is preferably between 1 and 40 g/100 ml depending of the molecular weight of each polymer. Most preferably, the concentration of each polymer is 25 g/100 ml or 25%. Equal concentrations of PVP and PEG generally provide the most favorable polymer mixture for the formation of a polysaccharide-protein conjugate. The volume of polymer added to the polysaccharide varies depending on the sizes and quantities of the polysaccharide and protein. Preferably, approximately three volumes of the polymer mixture are added to one volume of a solution containing the polysaccharide and protein. The pH of the macromolecular crowding agent is preferably between 4 and 9, most preferably pH 5.

The macromolecular crowding agent may be incubated with the oxidized polysaccharide and protein at a temperature between room temperature and 58° C. or at a series of different incubation temperatures within this range for a sufficient amount of time to allow formation of polysaccharide-protein microparticles. The preferred length of incubation time is between 30 minutes and 2 hours.

The microparticles may be separated from the other reagents in the incubation mixture by conventional methods well known to those skilled in the art such as centrifugation, filtration or decantation in combination with established washing procedures. The resulting Schiff base microparticles may then be resuspended in a physiologically-acceptable buffer such as a saline solution or phosphate buffered saline. The polysaccharide-protein conjugate may be administered as microparticles. Alternatively, the microparticles may be substantially dissolved with a base or in a solubilizing solvent, such as an alkaline solution, to produce a soluble Schiff base conjugate. The conjugate may then be diluted with a physiologically acceptable buffer. The preferred base is sodium hydroxide. The solubilized conjugate microparticles are believed to be more immunogenic than the conjugate microparticles that have not been substantially dissolved and may also be administered to induce an immune response. The solubilized conjugate preferably contains a small amount of microparticles. Thus, the solubilized conjugate preferably contains a sufficient amount of soluble antigen to prime an immune response in a human or animal and contains a sufficient amount: of the slow-releasing antigenic microparticles, which boost the immune response.

The polysaccharide-protein conjugate can be formulated and packaged, alone or in combination with other antigens, using methods and materials known to those skilled in he art for vaccines. The polysaccharide-protein conjugate is preferably added to the composite vaccine normally administered to infants. The polysaccharide-protein conjugate may be administered with an adjuvant in an amount effective to enhance the immunogenic response against the conjugate. At this time, the only adjuvant widely used in humans has been alum (aluminum phosphate or aluminum hydroxide). Saponin and its purified component Quil A, Freund's complete adjuvant and other adjuvants used in research and veterinary applications have toxicities which limit their potential use in human vaccines. However, chemically defined preparations such as muramyl dipeptide, monophosphoryl lipid A, phospholipid conjugates such as those described by Goodman-Snitkoff et al. *J. Immunol.* 147:410–415 (1991) and incorporated by reference herein, encapsulation of the conjugate within a proteoliposome as described by Miller et al., *J. Exp. Med.* 176:1739–1744 (1992) and incorporated by reference herein, and encapsulation of the protein in lipid vesicles such as Novasome™ lipid vesicles (Micro Vescular Systems, Inc., Nashua, N.H.) may also be useful.

Methods of administration and dose

In the preferred embodiment, the vaccine is packaged in a single dosage for immunization by parenteral (i.e., intramuscular, intradermal or subcutaneous) administration or nasopharyngeal (i.e., intranasal) administration. The conjugate is most preferably injected intramuscularly into the deltoid muscle. The conjugate is preferably combined with a pharmaceutically acceptable carrier to facilitate administration. The carrier is usually water or a buffered saline, with or without a preservative. The antigen may be lyophilized for resuspension at the time of administration or in solution.

The carrier may also be a polymeric delayed release system. Synthetic polymers are particularly useful in the formulation of a vaccine to effect the controlled release of antigens. For example, the polymerization of methyl methacrylate into spheres having diameters less than one micron has been reported by Kreuter, J., *Microcapsules and Nanoparticles in Medicine and Pharmacology*, M. Donbrow (Ed). CRC Press, p. 125–148.

Microencapsulation of the polysaccharide-protein will also give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters polyamides, poly (d,1-lactide-co-glycolide) (PLGA) and other biodegradable polymers. The use of PLGA for the controlled release of antigen is reviewed by Eldridge, J. H., et al. *Current Topics in Microbiology and Immunology*, 146:59–66 (1989).

The preferred dose for the human infant is a 1 ml injection containing between 5 and 25 μg of the polysaccharide-protein conjugate. Based on this range, equivalent dosages for heavier body weights can be determined. The polysaccharide-protein conjugate may additionally contain stabilizers such as thimerosal (ethyl(2-mercaptobenzoato-S)mercury sodium salt) (Sigma Chemical Company, St. Louis, Mo.) or physiologically acceptable preservatives.

The present invention will be further understood by reference to the following non-limiting example.

EXAMPLE 1

Preparation of Schiff Base Polysaccharide-protein Conjugate

An aliquot containing 0.125 ml of purified *Haemophilus influenzae* type b polysaccharide (24.5 mg/ml) was mixed with 0.125 ml of sodium periodate (8 mM in deionized water) (Sigma Chemical Company, St. Louis, Mo.) and incubated at room temperature for 30 minutes. 7.5 μl of ethylene glycol (Sigma Chemical Company, St. Louis, Mo.) was added and incubated at room temperature for 30 minutes. To the mixture was added 0.460 ml of purified tetanus toxoid (6.9 mg/ml) and 2.13 ml of a polymer mixture containing 25% polyvinylpyrrolidone (PVP, molecular weight 40,000), 25% polyethylene glycol (PEG, molecular weight 3,500), and sodium phosphate buffer, pH 5.0, while vortexing. The reaction mixture was incubated either a) at room temperature for one hour, b) at room temperature for 30 minutes and at 37° C. for 30 minutes, or c) at room temperature for 30 minutes, at 37° C. for 30 minutes and at 58° C. for 30 minutes. Schiff base microparticles formed. The mixture was centrifuged at 13,200 rpm for 20 minutes to pellet the microparticles. The supernatant was decanted and the microparticles washed twice with 1.0 ml of 25% ethanol and 1.0 ml of deionized water. The resulting *Haemophilus influenzae* type b-tetanus toxoid (Hib-TT) conjugate microparticles were injected into mice as described below. Alternatively, microparticles were suspended in 1.0 ml of deionized water, substantially dissolved in 0.1N NaOH, and diluted in phosphate buffer to produce a soluble Schiff base *Haemophilus influenzae* type b-tetanus toxoid (Hib-TT) conjugate and injected as follows.

A 0.2 ml aliquot of a 12.5 μg/ml saline solution of the Hib-TT conjugate (based on polysaccharide content) microparticles or solubilized Hib-TT conjugate microparticles was injected subcutaneously into CD-1 female mice (13–15 g) (8 groups of 10 mice). A boost was injected on day 28. Blood samples were taken for immunogenicity analysis on days 28, 42, and 70. The results are shown in Table 1. Group I was injected with the Hib-TT conjugate microparticles, whereas Group II was injected with the solubilized Hib-TT conjugate. The controls contained two different doses of a Hib-TT conjugate prepared, by reductive amination. The Hib+TT sample was not conjugated. The results demonstrate that the Hib-TT Schiff base conjugates are highly immungenic.

TABLE 1

Immunogenicity of Haemophilus Influenza Type b Polysaccharide (Hib)-Tetanus Toxoid (TT) Conjugates in mice after 1° and 2° doses.

| | Dose (μg) | | Geometric Mean Serum IgG Titers (μg/ml) | | | |
| | | | 4 wk post 1° | | 2 wk post 2° | |
| Group | Hib | TT | Hib | TT | Hib | TT |
| I | 2.5 | 30 | 0.4 | 28 | 2.5 | 1966 |
| II | 2.5 | 30 | 0.5 | 96 | 116.9 | 9199 |
| control | 2.5 | 6.4 | 0.5 | 30 | 2.1 | 738 |
| control | 11.8 | 30 | 0.9 | 147 | 2.2 | 225 |
| Hib + TT | 2.5 | 30 | 0.1 | 44 | 0.2 | 841 |

Modifications and variations of the method and kit for making a polysaccharide-protein Schiff base conjugate, will be obvious to those skilled in the art from the foregoing detailed description. Such modifications and variations are intended to come within the scope of the appended claims.

We claim:

1. A method for making a polysaccharide-protein conjugate comprising:
   a) oxidizing a polysaccharide with an oxidizing agent to form an oxidized polysaccharide, and
   b) combining the oxidized polysaccharide with a protein in the presence of a macromolecular crowding agent wherein the polysaccharide and protein form a Schiff base conjugate in the absence of a reducing agent.

2. The method of claim 1 wherein the macromolecular crowding agent is a soluble linear polymer.

3. The method of claim 1 wherein the soluble linear polymer is a compound selected from the group consisting of polyvinylpyrrolidone, polyethylene glycol, dextran, nonylphenol-ethoxylates, polyvinyl alcohol, and mixtures thereof.

4. The method of claim 1 wherein the macromolecular crowding agent is a mixture of polyvinylpyrrolidone and polyethylene glycol.

5. The method of claim 4 wherein the molecular weight of the polyvinylpyrrolidone is approximately 40,000.

6. The method of claim 4 wherein the molecular weight of the polyethylene glycol is 3500.

7. The method of claim 4 wherein the polysaccharide and protein form a Schiff base microparticle.

8. The method of claim 7 further comprising dissolving the microparticle.

9. The method of claim 8 wherein the microparticle is dissolved with a base.

10. The method of claim 1 wherein the oxidizing agent is selected from the group consisting of lead tetra-acetate, periodic acid, and sodium periodate.

11. The method of claim 1 further comprising quenching the oxidizing agent with a quenching reagent.

12. The method of claim 1 wherein the quenching reagent is an alcohol.

13. The method of claim 1 wherein the polysaccharide is derived from a bacteria selected from the group consisting of *Haemophilus influenza*, pneumococci, meningococci, β-hemolytic streptococci, *Escherichia coli*, *Pseudomonas aeruginosa*, Klebsiella, and Vibrio cholerae.

14. The method of claim 1 wherein the protein is selected from the group consisting of tetanus toxoid, diphtheria toxoid, *Neisseria meningitidis* outer membrane protein, a nontoxic cross-reacting mutant of diphtheria toxin, a protein isolated from bacteria, and a synthetic protein containing lysine residues.

15. The method of claim 1 wherein the polysaccharide and protein form a Schiff base conjugate microparticle that yields solubilized conjugate when the microparticle is dissolved.

16. A kit for making a polysaccharide-protein conjugate consisting essentially of:
   a) an oxidizing agent for oxidizing a polysaccharide,
   b) a protein,
   c) a soluble linear polymer macromolecular crowding agent, and,
   d) a base.

17. The kit of claim 16 wherein the oxidizing agent is selected from the group consisting of lead tetra-acetate, periodic acid, and sodium periodate.

18. The kit of claim 16 further comprising quenching reagent for quenching the oxidizing agent.

19. The kit of claim 16 wherein the protein is a carrier protein selected from the group consisting of tetanus toxoid, diphtheria toxoid, *Neisseria meningitidis* outer membrane protein, a nontoxic cross-reacting mutant of diphtheria toxin, a protein isolated from bacteria, and a synthetic protein containing lysine residues.

20. The kit of claim 16 wherein the macromolecular crowding agent is a mixture of polyvinylpyrrolidone and polyethylene glycol.

21. The kit of claim 16 further comprising a base for dissolving polysaccharide-protein conjugate microparticles.

22. A polysaccharide-protein conjugate prepared by a method comprising:
   a) oxidizing a polysaccharide with an oxidizing agent to form an oxidized polysaccharide and
   b) combining the oxidized polysaccharide with a protein in the presence of a macromolecular crowding agent,
   wherein the polysaccharide and protein form a Schiff base conjugate in the absence of a reducing agent.

23. The conjugate of claim 22 prepared by a method wherein the polysaccharide and protein form a Schiff base conjugate microparticle that yields solubilized conjugate when the microparticle is dissolved.

24. The conjugate of claim 22 prepared by a method wherein the macromolecular crowding agent is a soluble linear polymer.

25. The conjugate of claim 22 of claim 1 prepared by a method wherein the soluble linear polymer is a compound selected from the group consisting of polyvinylpyrrolidone, polyethylene glycol, dextran, nonylphenol-ethoxylates, polyvinyl alcohol, and mixtures thereof.

26. The conjugate of claim 22 of claim 1 prepared by a method wherein the macromolecular crowding agent is a mixture of polyvinylpyrrolidone and polyethylene glycol.

27. The conjugate of claim 23 wherein the method further comprises dissolving the microparticle.

28. The conjugate of claim 26 prepared by a method wherein the microparticle is dissolved with a base.

29. A method for making a polysaccharide-protein conjugate microparticle comprising:
   a) oxidizing a polysaccharide with an oxidizing agent to form an oxidized polysaccharide, and
   b) combining the oxidized polysaccharide with a protein in the presence of a macromolecular crowding agent wherein the polysaccharide and protein form a Schiff base conjugate microparticle.

30. A polysaccharide-protein conjugate microparticle prepared by a method comprising:
   a) oxidizing a polysaccharide with an oxidizing agent, and
   b) combining the oxidized polysaccharide with a protein in the presence of a macromolecular crowding agent, wherein the polysaccharide and protein form a Schiff base conjugate.

* * * * *